United States Patent [19]

Wirth et al.

[11] Patent Number: 5,789,383
[45] Date of Patent: Aug. 4, 1998

[54] BRADYKININ ANTAGONISTS FOR THE PROPHYLAXIS OR TREATMENT OF VIRUS DISEASES

[75] Inventors: Klaus Wirth, Kriftel; Irvin Winkler, Liederbach; Fred Lembeck, Graz; Gerhard Breipohl, Frankurt; Stephan Henke, Hofheim; Jochen Knolle, Kriftel, all of Germany

[73] Assignee: Hoechst Aktiengesellschaft, Frankfurt am Main, Germany

[21] Appl. No.: 366,598

[22] Filed: Dec. 29, 1994

[30] Foreign Application Priority Data

Dec. 31, 1993 [DE] Germany ............... 43 45 062.8

[51] Int. Cl.$^6$ ............... A61K 38/00; A61K 38/02; C07K 5/00; C07K 7/00
[52] U.S. Cl. ............... 514/15; 514/16; 530/314
[58] Field of Search ............... 514/15, 16; 530/314, 530/300, 328

[56] References Cited

U.S. PATENT DOCUMENTS 5,422,097  6/1995  Gwaltney, Jr. ............... 424/45

FOREIGN PATENT DOCUMENTS

| 0 370 453 A3 | 11/1989 | European Pat. Off. |
| 0370453 | 11/1989 | European Pat. Off. ......... C07K 7/18 |
| 0 370 453 | 5/1990 | European Pat. Off. |
| 0472220 | 8/1991 | European Pat. Off. ......... C07K 7/18 |
| 0 472 220 A1 | 2/1992 | European Pat. Off. |
| 9217201 | 10/1992 | WIPO ............... A61K 37/42 |
| 9218155 | 10/1992 | WIPO ............... A61K 37/42 |
| 9218156 | 10/1992 | WIPO ............... A61K 37/42 |
| WO 92/17201 | 10/1992 | WIPO |
| WO 92/18155 | 10/1992 | WIPO |
| WO 92/18156 | 10/1992 | WIPO |

OTHER PUBLICATIONS

E. Sandström et al., "Antiviral Therapy in Human Immunodeficiency Virus Infections. Current Status (Part I)," Drugs 45(4): 488–508 (1993).

E. Sandström et al., "Antiviral Therapy in Human Immunodeficiency Virus Infections, Current Status (Part II)," Drugs 45(5): 637–653 (1993).

Stewart, John M. et al., "Bradykinin Antagonists: Design and Applications," J. Cell. Bio., Abstracts, Supp. 14C, p. 226 (1990).

Kyle D. J. et al., "Recent advances toward novel bradykinin antagonists," Drugs of the Future, vol. 17, No. 4, pp. 305–312 (1992).

Trifilieff, A. et al., "Kinins and respiratory tract diseases," Eur. Respir. J. 6:576–87 (1993).

Higgins, P.G., et al., "A study of the efficacy of the bradykinin antagonist, NPC 567, in rhinovirus infections in human volunteers," Antiviral Research 14: 339–344 (1990).

"Kinins and their antagonists," The Lancet, 338: 287–88 1991.

Greaves, M.W., "Inflammation and mediators," British Journal of Dermatology, 119:419–426, 1988.

Higgins et al., *Antiviral Research*, vol. 14, pp. 339–344, 1990.

*Primary Examiner*—Avis M. Davenport
*Attorney, Agent, or Firm*—Finnegan, Henderson, Farabow, Garrett & Dunner, L.L.P.

[57] ABSTRACT

Bradykinin antagonists and their physiologically tolerated salts are suitable for the treatment or prophylaxis of virus diseases.

15 Claims, No Drawings

BRADYKININ ANTAGONISTS FOR THE PROPHYLAXIS OR TREATMENT OF VIRUS DISEASES

The invention relates to the use of bradykinin antagonists for the preparation of medicaments for the treatment of virus diseases.

Bradykinin and related peptides are potent inflammation- and pain-generating and vasoactive endogenous substances. The use of bradykinin antagonists as agents for combating states mediated, induced or assisted by bradykinin is known (EP 0370453).

Surprisingly, it has now been found that bradykinin antagonists are suitable agents for the treatment of virus diseases.

Particularly suitable bradykinin antagonists are, inter alia, the peptides of the formula I

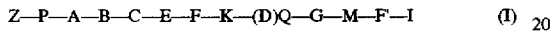
$$Z-P-A-B-C-E-F-K-(D)Q-G-M-F'-I \qquad (I)$$

in which:

Z is a₁) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl, or $(C_1-C_8)$-alkylsulfonyl, in which in each case 1, 2 or 3 hydrogen atoms are optionally replaced by 1, 2 or 3 identical or different radicals from the series comprising carboxyl, NHR(1), $[(C_1-C_4)$-alkyl$]$NR(1) or $[(C_6-C_{10})$-aryl-$(C_1-C_4)$-alkyl$]$NR(1), in which R(1) is hydrogen or a urethane protective group, $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-$[(C_6-C_{10})$-aryl-$(C_1-C_4)]$-alkylamino, carbamoyl, phthalimido, 1,8-naphthalimido, sulfamoyl, $(C_1-C_4)$-alkoxycarbonyl, $(C_6-C_{14})$-aryl and $(C_6-C_{14})$-aryl-$(C_1-C_5)$-alkyl, or in which in each case 1 hydrogen atom is optionally replaced by a radical from the series comprising $(C_3-C_8)$-cycloalkyl, $(C_1-C_6)$-alkyl-sulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy and 1 or 2 hydrogen atoms are replaced by 1 or 2 identical or different radicals from the series comprising carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

a₂) $(C_6-C_4)$-aryl, $(C_7-C_{15})$-aroyl, $(C_6-C_{14})$-arylsulfonyl, $(C_3-C_{13})$-heteroaryl or $(C_3-C_{13})$-heteroaroyl;

a₃) carbamoyl, which can optionally be substituted on the nitrogen by $(C_1-C_8)$-alkyl, $(C_6-C_{14})$-aryl or $(C_6-C_{14})$-aryl-$(C_1-C_5)$-alkyl;

and in which, in the radicals defined under a₁), a₂) and a₃), the aryl, heteroaryl, aroyl, arylsulfonyl and heteroaroyl groups are optionally substituted by 1, 2, 3, or 4 radicals from the series comprising carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or a radical of the formula II

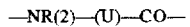
$$—NR(2)—(U)—CO— \qquad (II)$$

in which

R(2) is hydrogen, methyl or a urethane protective group,

U is $(C_3-C_8)$-cycloalkylidene, $(C_6-C_{14})$-arylidene, $(C_3-C_{13})$-heteroarylidene or $(C_6-C_{14})$-aryl-$(C_1-C_6)$-alkylidene, which can optionally be substituted, or $[CHR(3)]_n$, in which n is 1–8, preferably 1–6, the radicals R(3) independently of one another are hydrogen, $(C_1-C_6)$-alkyl, $(C_3-C_8)$-cycloalkyl, $(C_6-C_{14})$-aryl or $(C_3-C_{13})$-heteroaryl, which, with the exception of the hydrogen, are in each case optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, in which substituted amino is preferably —N(A')—Z, substituted amidino is preferably —(NH═)C—NH—Z, substituted guanidino is preferably —N(A') —C[═N(A')]—NH—Z and substituted ureido is preferably —CO—N(A')—Z, in which the radicals A' independently of one another are hydrogen or Z, in which Z is as defined under a₁) or a₂);

or in which R(2) and R(3), together with the atoms carrying these, form a mono-, bi- or tricyclic ring system having 2 to 15 carbon atoms;

A is as defined for P;

B is a basic amino acid in the L- or D-configuration, which can be substituted in the side chain;

C is a compound of the formula IIIa or IIIb

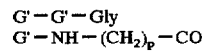
$$G'—G'—Gly \qquad (IIIa)$$
$$G'—NH—(CH_2)_p—CO \qquad (IIIb)$$

in which p is 2 to 8 and the radicals G' independently of one another are a radical of the formula IV

$$—NR(4)—CHR(5)—CO— \qquad (IV)$$

in which

R(4) and R(5), together with the atoms carrying these, form a heterocyclic mono-, bi- or tricyclic ring system having 2 to 15 carbon atoms;

E is the radical of a neutral, acid or basic, aliphatic or alicyclic-aliphatic amino acid;

the radicals F independently of one another are the radical of a neutral, acid or basic, aliphatic or aromatic amino acid, which can be substituted in the side chain, or a direct bond;

(D)Q is D-Tic, D-Phe, D-Dic, D-Thi or D-Nal, which can optionally be substituted by halogen, methyl or methoxy, or a radical of the following formula (V)

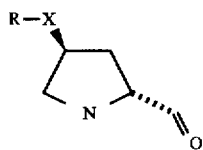 (V)

in which

X is oxygen or sulfur or a direct bond;

R is hydrogen, $(C_1-C_8)$-alkyl, $(C_3-C_8)$-cycloalkyl, $(C_6-C_{14})$-aryl or $(C_6-C_{14})$-aryl-$(C_1-C_4)$-alkyl, in which the alicyclic radical can optionally be substituted by halogen, methyl or methoxy;

G is as defined above for G' or a direct bond;

F is as defined for F, a radical —NH—$(CH_2)_q$—, where q=2 to 8, or, if G is not a direct bond, a direct bond;

I is —OH, —$NH_2$ or $NHC_2H_5$;

K is the radical —NH—$(CH_2)_x$—CO— where x=1 to 4, or a direct bond and

M is as defined for F, and physiologically tolerated salts thereof.

Suitable bradykinin antagonists are described, for example, in the Patent Publications EP 370 453, EP 472 220, WO 92/18155, WO 92/18156 and WO 92/17201 [Cortech; bradykinin antagonists of the formula $X(BKA)_n$, in which X is a bonding member, BKA is the peptide chain of a bradykinin antagonist and n is an integer greater than 1; bradykinin antagonists of the formula X(BKA); and bradykinin antagonists of the formula (Y)(X)(BKA) where Y is a ligand which is an antagonist or an agonist for a non-bradykinin receptor].

Particularly suitable peptides of the formula I are those in which:

Z is hydrogen or is as defined under $a_1$), $a_2$) or $a_3$),

P is a bond or a radical of the formula II

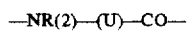 (II)

where

U is CHR(3) and R(3) is as defined above,

R(2) is H or $CH_3$,

A is a bond.

Particularly preferred compounds of the formula I are those in which:

Z is hydrogen or is as defined under $a_1$), $a_2$) or $a_3$),

P is a bond or a radical of the formula II

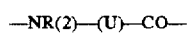 (II)

where

U is CHR(3) and where the radicals R(3) independently of one another are hydrogen, $(C_1-C_6)$-alkyl, $(C_3-C_8)$-cycloalkyl, $(C_6-C_{14})$-aryl or $(C_3-C_{13})$-heteroaryl, which, with the exception of the hydrogen, are in each case optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, and in which substituted amino is preferably —N(A') —Z and substituted guanidino is preferably —N(A') —C|=N(A')|—NH—Z, in which the radicals A' independently of one another are hydrogen or Z, in which Z is as defined under $a_1$) or $a_2$);

or in which R(2) and R(3), together with the atoms carrying these, form a mono-, bi- or tricyclic ring system having 2 to 15 carbon atoms;

R(2) is H or $CH_3$,

A is a bond, (D)Q is D-Tic.

(R)-Arginyl-(S)-arginyl-(S)-prolyl-(2S,4R)-hydroxyprolyl)glycyl-(S)-|3-(2-thienyl)alanyl|-(S)-seryl-(R)-|(1,2,3,4-tetrahydro-3-isoquinolyl)carbonyl|-(2S,3aS,7aS)-|(hexahydro-2-indolinyl)carbonyl|-(S)-arginine N-acetate, which carries the INN name icatibant acetate and is also called HOE 140, is especially suitable.

The present invention furthermore relates to combination preparations which comprise, in addition to a bradykinin antagonist, at least one other antiviral agent. The particular advantage of these combination preparations lies in the fact that the action of the viruses (for example skin lesions) and also the spread of the viruses are combated with particular persistence.

Various other antiviral agents can be employed according to the invention, such as, for example, acyclovir, Val-acyclovir, pencyclovir, BVA-uracil, vidarabine, iododeoxyuridine, broravir, zidovudine (AZT), didanosine (DDI), dideoxycytidine (DDC) and lamivudine (3-TC), in particular acyclovir. The compounds mentioned are commercially obtainable or can be prepared by generally known processes (cf. Merck Index, 11th Edition Rahway, N.J. 1989, Drugs 45 (4), 488 et seq., 45 (5), 637 et seq., 1993).

The abovementioned preferred bradykinin antagonists are likewise preferred for the combination preparations mentioned. A particularly preferred combination preparation comprises HOE 140 and acyclovir or equivalents or prodrugs thereof.

The abovementioned compounds and combination preparations can be employed according to the invention against various viral diseases. They are of particular importance for combating herpes viruses (for example HSV-1, HSV-2, HSV-3, VSV) and for the recurrence of varicella zoster viruses (VSV).

The bradykinin antagonists are used in a suitable administration form as medicaments for the treatment of virus diseases.

Suitable pharmaceutical preparations comprise an active amount of the bradykinin antagonist—individually or in combination—together with an inorganic or organic pharmaceutically usable excipient and if appropriate together with one or more other antiviral agents.

The preparation can be used enterally, parenterally—such as, for example, subcutaneously, intramuscularly or intravenously—sublingually, epicutaneously, nasally, rectally, intravaginally, intrabuccally or by inhalation. The dosage of the active compound depends on the warm-blooded species, the body weight, age and the method of administration.

The pharmaceutical preparations of the present invention are prepared in solution, mixing, granulating or tablet-coating processes which are known per se.

For the oral use form or for application to the mucosae, the active compounds are mixed with the additives customary for this purpose, such as excipients, stabilizers or inert diluents, and are brought by customary methods into suitable dosage forms, such as tablets, coated tablets, hard gelatin capsules, aqueous, alcoholic or oily suspensions or aqueous, alcoholic or oily solutions. Inert excipients which can be used, are, for example, gum arabic, magnesia, magnesium carbonate, potassium phosphate, lactose, glucose, magnesium stearyl fumarate or starch, in particular corn starch. Formulation can thus be effected in either dry or moist granule form. Possible oily excipients or solvents are, for example, vegetable or animal oils, such as sunflower oil and cod-liver oil.

A preparation for topical use can be in the form of an aqueous or oily solution, lotion, emulsion or jelly, ointment or greasy ointment or, if possible, in spray form, it being possible to improve the adhesion, if appropriate, by addition of a polymer.

For the intranasal use form, the compounds are mixed with the additives customary for this purpose, such as stabilizers or inert diluents, and brought by customary methods into suitable dosage forms, such as aqueous, alcoholic or oily suspensions or aqueous, alcoholic or oily suspensions or aqueous, alcoholic or oily solutions. Chelating agents, ethylenediamine-N,N,N',N'-tetraacetic acid, citric acid, tartaric acid or salts thereof can be added to aqueous intranasal formulations. The nasal solutions can be administer ed by means of metered atomizers, or as nasal drops with a viscosity-increasing content or nasal gels or nasal creams.

Nebulizers or compressed gas packs using inert carrier gases can be utilized for inhalative use.

For intravenous, subcutaneous, epicutaneous or intradermal administration, the active compounds or physiologically tolerated salts thereof are dissolved, suspended or emulsified, if desired with the pharmaceutically customary auxiliaries, for example for isotonicizing or pH adjustment, as well as solubilizing agents, emulsifiers or other auxiliaries.

Because of the short half-lives of some of the medicaments described in body fluids, it is appropriate to use injectable sustained release formulations. Medicament forms which can be used are, for example, oily crystal suspensions, microcapsules, rods or implants, it being possible for the latter to be built up from tissue-tolerated polymers, in particular biodegradable polymers, such as, for example, those based on polylactic acid/polyglycolic acid copolymers or human albumin.

Topical administration is of particular importance for the compounds which can be used according to the invention and for the combination preparations which can be employed according to the invention.

The active dose is at least 0.001 mg/kg/day, preferably at least 0.01 mg/kg/day, in particular at least 0.1 mg/kg/day to not more than 3 mg/kg/day, preferably to not more than 1 mg/day/kg of body weight, based on an adult weighing 75 kg. The other antiviral agent is preferably employed, if appropriate, in its known dosage range.

The ratio of the amounts of bradykinin antagonist to other antiviral agent can extend over a wide range. A ratio of 1:100 to 100:1 is preferred.

The present invention is to be explained in more detail by the embodiment example below and by the content of the patent claims.

EXAMPLE 1

Testing of the Action of HOE 140 on Skin Lesions Caused by HSV-1 in Hairless Mice Procedure:

To investigate the antiviral efficacy, immunocompetent hairless mice (hr/hr) were scarified on one side of the body with the aid of a glass fiber stick and infected by rubbing in a virus suspension (HSV-1, clinical isolate "corneae") in a dilution of 1/100. The infected animals were divided into the various test groups and housed individually in Makrolon cages.

For the topical treatment, the preparation was incorporated into a neutral cream formulation (oil-in-water emulsion) in the concentrations stated below. Treatment took place by rubbing about 50 mg of cream into the infected area twice daily from the 4th to the 14th day after infection.

For the systemic treatment, the preparation was dissolved in 0.9% NaCl and administered subcutaneously twice daily from the 4th to 14th day after infection.

The evaluation criteria used were the severity of the skin lesions caused by the virus, and the number of surviving animals and the average period of survival of the animals which died.

Result:

The results are summarized in the following table:

Investigation of the action of HOE 140 on skin lesions caused by HSV-1 on hairless mice (12/93). Treatment 2× daily for 10 days, starting 4 days after cutaneous infection of the scarified dorsal skin.

| Dose | Survivors/group size | Average survival time (days) | Animals with zoster formation |
|---|---|---|---|
| 1% topically | 3/5 | 9.0 ± 1.4 | 1 |
| 5% topically | 2/5 | 9.0 ± 2.0 | 2 |
| 1 mg/kg s.c. | 3/5 | 8.0 ± 0 | 1 |
| 5 mg/kg s.c. | 2/5 | 8.0 ± 0 | 0 |
| control | 1/6 | 9.3 ± 1.5 | 5 |

The development of severe skin lesions (zoster formation) was significantly ($p<0.001$, $Chi^2$ test) lower in the treated animals than in the untreated controls, while the survival rate was influenced less (not significant, $Chi^2$ test).

The present experiments show that both the parenteral (subcutaneous) and the topical treatment with HOE 140 cause a significant reduction in the symptoms of a cutaneous herpes infection.

| Four-field test | | | |
|---|---|---|---|
| | Result | | |
| Condition | positive | negative | Total |
| Treatment | 16 | 4 | 20 |
| Control | 1 | 5 | 6 |
| Total | 17 | 9 | 26 |
| $CHI^2$ 8.18 | | | |
| Exceeding probability (P %) | 5 | 1 | 0.1 |
| $CHI^2$ distribution, two-sided test | 3.84 | 6.63 | 10.83 |
| One-sided test | 1.92 | 3.32 | 5.42 |

EXAMPLE 2

Investigation of the Action of HOE 140 on Skin Lesions Caused by HSV-1 in Hairless Mice in Combination with Acyclovir HOE 140 was administered twice daily either topically as a 2% strength cream in a neutral base or subcutaneously with 2 mg/kg per dosage. Acyclovir was administered as a 0.05% strength solution in the drinking water. To demonstrate superiority of the combination treatment, the infection intensity and dosage of the substances were chosen such that the treatment with the individual substances was suboptimum.

Experiment 22/94:
Administration of acyclovir day 0–7
Administration of HOE 140 day 3–8

| Dose of HOE 140 topically or s.c. | Acyclovir orally | Survivors/ group size | Average survival time (days) | Animals with zoster formation |
|---|---|---|---|---|
| 12 × 2% | | 2/8 | 8.3 ± 1.0 | 7 |
| 12 × 2 mg/kg s.c. | | 3/8 | 9.4 ± 1.3 | 5 |
| 12 × 2% | 0.05% | 5/8 | 10.0 ± 1.7 | 3 |
| 12 × 2 mg/kg s.c. | 0.05% | 8** | | 0 |
| 12 × 0% | | 0/8 | 9.6 ± 1.2 | 4 |

**p (Chi² test) < 0.01 compared with the control

The mortality rate and the formation of severe skin lesions (zoster formation) were reduced with the combination treatment.

Experiment 24/94:
Administration of acyclovir day 3–7
Administration of HOE 140 day 3–7 or 0–7

| Dose of HOE 140 topically or s.c. | Acyclovir orally | Survivors/ group size | Average survival time (days) | Animals with zoster formation |
|---|---|---|---|---|
| 10 × 2 | — | 0/8* | $7.8 \pm 0.5^1$ | 8 |
| — | 0.05% | 2/8* | 7.3 ± 1.2 | 7 |
| 10 × 2 | 0.05% | 3/8* | $9.0 \pm 0.7^{1,2}$ | 8 |
| 16 × 2 | 0.05% | 1/8* | $8.6 \pm 1.0^{1,2}$ | 8 |
| 10 × 0% | — | 0/9 | 7.1 ± 0.9 | 9 |

$^1$p (t-test) < 0.05 compared with the control
$^2$p (t-test) < 0.05 compared with acyclovir alone
*p (chi² test) not significant In a second combination experiment, it was confirmed that combination of HOE 140 with acyclovir is superior to treatment with HOE 140 or acyclovir under the same experimental conditions. While no significant differences in the survival rate occurred in this experiment, the survival time of the animals with the combination treatment was increased significantly compared with the other forms of treatment and the untreated control.

We claim:

1. A method of treatment for a host suffering from herpes or varicella zoster comprising the step of administering a bradykinin antagonist, or a physiologically tolerated salt thereof, to the host in need thereof.

2. The method of claim 1, further comprising the step of administering the bradykinin antagonist, or a physiologically tolerated salt thereof, in conjunction with another antiviral agent to the host in need thereof, whereby a synergistic treatment effect is achieved.

3. The method as claimed in claim 1, in which the bradykinin antagonist is a compound of the formula I,

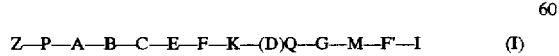

Z—P—A—B—C—E—F—K—(D)Q—G—M—F'—I    (I)

in which:
Z is
a₁) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl, or $(C_1-C_8)$-alkyl-sulfonyl, in which in each case 1, 2 or 3 hydrogen atoms are optionally replaced by 1, 2 or 3 identical or different radicals from the group consisting of $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-[$(C_6-C_{10})$-aryl-$(C_1-C_4)$]-alkylamino, carbamoyl, phthalimido, 1,8-naphthalimido, sulfamoyl, $(C_1-C_4)$-alkoxycarbonyl, $(C_6-C_{14})$-aryl, $(C_6-C_{14})$-aryl-$(C_1-C_5)$-alkyl, carboxyl, NHR(1), [$(C_1-C_4)$-alkyl]-NR(1) and [$(C_6-C_{10})$-aryl-$(C_1-C_4)$-alkyl]NR(1),
in which R(1) is hydrogen or a urethane protective group, or
in which in each case 1 hydrogen atom is optionally replaced by a radical from the group consisting of $(C_3-C_8)$-cycloalkyl, $(C_1-C_6)$-alkylsulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy,
and
1 or 2 hydrogen atoms are replaced by 1 or 2 identical or different radicals from the group consisting of carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

a₂) $(C_6-C_{14})$-aryl, $(C_7-C_{15})$-aroyl, $(C_6-C_{14})$-arylsulfonyl, $(C_3-C_{13})$-heteroaryl or $(C_3-C_{13})$-heteroaroyl; or a₃) carbamoyl, which can optionally be substituted on the nitrogen by $(C_1-C_8)$-alkyl, $(C_6-C_{14})$-aryl or $(C_6-C_{14})$-aryl-$(C_1-C_5)$-alkyl;

and in which, in the radicals defined under a₁), a₂) and a₃), the aryl, heteroaryl, aroyl, arylsulfonyl and heteroaroyl groups are optionally substituted by 1, 2, 3, or 4 radicals from the group consisting of carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or is a radial of the formula II,

—NR(2)—(U)—CO—    (II)

in which;
R(2) is hydrogen, methyl or a urethane protective group;
U is $(C_3-C_8)$-cycloalkylidene, $(C_6-C_{14})$-arylidene, $(C_3-C_{13})$-heteroarylidene or $(C_6-C_{14})$-aryl-$(C_1-C_6)$-alkylidene, which can optionally be substituted, or
[CHR(3)]ₙ, in which,
n is 1–8;
the radicals R(3) independently of one another are hydrogen, $(C_1-C_6)$-alkyl, $(C_3-C_8)$-cycloalkyl, $(C_6-C_{14})$-aryl or $(C_3-C_{13})$-heteroaryl, which, with the exception of the hydrogen, are in each case unsubstituted or monosubstituted by amino, substituted amino, amidino, substituted amidino, hydroxyl, carboxyl, carbamoyl, guanidino, substituted guanidino, ureido, substituted ureido, mercapto, methyl-mercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, or in which R(2) and R(3), together with the atoms carrying these, form a mono-, bi- or tricyclic ring system having 2 to 15 carbon atoms;

A is as defined for P;

B is a basic amino acid in the L- or D-configuration, which can be substituted in the side chain;

C is a compound of the formula IIIa or IIIb $$G'-G'-Gly \qquad (IIIa)$$
$$G'-NH-(CH_2)_p-CO \qquad (IIIb)$$

in which, p is 2 to 8 and the radicals G' independently of one another are a radical of the formula IV $$-NR(4)-CHR(5)-CO- \qquad (IV)$$

in which,

R(4) and R(5), together with the atoms carrying these, form a heterocyclic mono-, bi or tricyclic ring system having 2 to 15 carbon atoms;

E is the radical of a neutral, acid or basic, aliphatic or alicyclic-aliphatic amino acid;

the radicals F independently of one another are a radical of a neutral, acid or basic, aliphatic or aromatic amino acid, which can be substituted in the side chain, or a direct bond;

(D)Q is D-Tic, D-Phe, D-Dic, D-Thi or D-Nal, which can optionally be substituted by halogen, methyl or methoxy, or a radical of the formula (V)

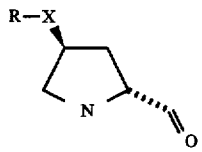

in which;

X is oxygen, sulfur or a direct bond;

R is hydrogen, $(C_1-C_8)$-alkyl, $(C_3-C_8)$-cycloalkyl, $(C_6-C_{14})$-aryl or $(C_6-C_{14})$-aryl-$(C_1-C_4)$-alkyl, in which the alicyclic radical can optionally be substituted by halogen, methyl or methoxy;

G is as defined above for G' or a direct bond;

F' is as defined above for F, a radical $-NH-(CH_2)_q-$ where q is 2 to 8, or, if G is not a direct bond, a direct bond;

I is $-OH$, $-NH_2$ or $NHC_2H_5$;

K is a radical $-NH(CH_2)_x-CO-$ where x is 1 to 4, or a direct bond; and

M is as defined above for F;

or a physiologically tolerated salt thereof.

4. A composition comprising at least one bradykinin antagonist, or a physiologically tolerated salt thereof, and at least one other antiviral agent.

5. The composition of claim 4, wherein the bradykinin antagonist is (R)-arginyl-(S)-arginyl-(S)-prolyl-(2S, 4R)-hydroxyprolyl)glycyl-(S)-|3-(2-thienyl)alanyl|-(S)-seryl-(R)-|(1,2,3,4-tetra-hydro-3-isoquinolyl)carbonyl|-(2S ,3aS, 7aS)-|(hexahydro-2-indolinyl)carbonyl|-(S)-arginine N-acetate, or a physiologically tolerated salt thereof.

6. A process for the preparation of the composition of claim 4, comprising the step of combining the bradykinin antagonist, or a physiologically tolerated salt thereof, and the other antiviral agent.

7. The process of claim 6, wherein the bradykinin antagonist is (R)-arginyl-(S)-arginyl-(S)-prolyl-(2S, 4R)-hydroxyprolyl)glycyl-(S)-|3-(2-thienyl)alanyl|-(S)-seryl-(R)-|(1,2,3,4-tetra-hydro-3-isoquinolyl)carbonyl|-(2S,3aS, 7aS)-|(hexahydro-2-indolinyl)carbonyl|-(S)-arginine N-acetate.

8. The method as claimed in claim 3, wherein the bradykinin antagonist is (R)-arginyl-(S)-arginyl-(S)-prolyl-(2S, 4R)-hydroxyprolyl)glycyl-(S)-|3-(2-thienyl)alanyl|-(S)-seryl-(R)-|(1,2,3,4-tetra-hydro-3-isoquinolyl)carbonyl|-(2S, 3aS,7aS)-|(hexahydro-2-indolinyl)carbonyl|-(S)-arginine N-acetate, or a physiologically tolerated salt thereof.

9. The method as claimed in claim 3, wherein the bradykinin antagonist is a compound of the formula I in which:

Z is hydrogen or is as defined under $a_1$), $a_2$) or $a_3$);

P is a bond or a radical of the formula II.

$$-NR(2)-(U)-CO- \qquad (II)$$

where

U is CHR(3) and R(3) is as defined;

R(2) is H or $CH_3$; and

A is a bond;

or a physiologically tolerated salt thereof.

10. The method as claimed in claim 3, wherein the bradykinin antagonist is a compound of the formula I in which:

Z is hydrogen or is as defined under $a_1$), $a_2$) or $a_3$);

P is a bond or a radical of the formula II.

$$-NR(2)-(U)-CO- \qquad (II)$$

where

U is CHR(3), and where the radicals R(3) independently of one another are hydrogen, $(C_1-C_6)$-alkyl, $(C_3-C_8)$-cycloalkyl, $(C_6-C_{14})$-aryl or $(C_3-C_{13})$-heteroaryl, which, with the exception of the hydrogen, are in each case unsubstituted or monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, or in which R(2) and R(3), together with the atoms carrying these, form a mono-, bi- or tricyclic ring system having 2 to 15 carbon atoms;

R(2) is H or $CH_3$;

A is a bond; and (D)Q is D-Tic;

or a physiologically tolerated salt thereof.

11. The method as claimed in claim 3, which n is 1–6.

12. The method as claimed in claim 3, in which the substituted amino is $-N(A')-Z$, the substituted amidino is $-(NH=)C-NH-Z$, the substituted guanidino is $-N(A')-C[=N(A')]-NH-Z$ and the substituted ureido is $-CO-N(A')-Z$, in which the radicals A' independently of one another are hydrogen or Z, in which Z is as defined under $a_1$) or $a_2$).

13. The method as claimed in claim 10, in which the substituted amino is —N(A')—Z and the substituted guanidino is —N(A')—C[=N(A')]—NH—Z, in which the radicals A' independently of one another are hydrogen or Z, in which Z is as defined under $a_1$) or $a_2$).

14. The composition of claim 4, in which the bradykinin antagonist is a compond of the formula I.

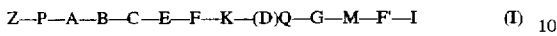

in which:

Z is $a_1$) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl, or $(C_1-C_8)$-alkyl-sulfonyl, in which in each case 1, 2 or 3 hydrogen atoms are optionally replaced by 1, 2 or 3 identical or different radicals from the group consisting of $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-[$(C_6-C_{10})$-aryl-$(C_1-C_4)$]-alkylamino, carbamoyl, phthalimido, 1,8-naphthalimido, sulfamoyl, $(C_1-C_4)$-alkoxycarbonyl, $(C_6-C_{14})$-aryl, $(C_6-C_{14})$-aryl-$(C_1-C_5)$-alkyl, carboxyl, NHR(1), [$(C_1-C_4)$-alkyl]-NR(1) and [$(C_6-C_{10})$-aryl-$(C_1-C_4)$-alkyl]N R(1), in which R(1) is hydrogen or a urethane protective group, or in which in each case 1 hydrogen atom is optionally replaced by a radical from the group consisting of $(C_3-C_8)$-cycloalkyl, $(C_1-C_6)$-alkylsulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy, and 1 or 2 hydrogen atoms are replaced by 1 or 2 identical or different radicals from the group consisting of carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

$a_2$) $(C_6-C_{14})$-aryl, $(C_7-C_{15})$-aroyl, $(C_6-C_{14})$-arylsulfonyl, $(C_3-C_{13})$-heteroaryl or $(C_3-C_{13})$-heteroaroyl; or $a_3$) carbamoyl, which can optionally be substituted on the nitrogen by $(C_1-C_8)$-alkyl, $(C_6-C_{14})$-aryl or $(C_6-C_{14})$-aryl-$(C_1-C_5)$-alkyl;

and in which, in the radicals defined under $a_1$), $a_2$) and $a_3$), the aryl, heteroaryl, aroyl, arylsulfonyl and heteroaroyl groups are optionally substituted by 1, 2, 3, or 4 radicals from the group consisting of carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or is a radial of the formula II.

in which:

R(2) is hydrogen, methyl or a urethane protective group;

U is $(C_3-C_8)$-cycloalkylidene, $(C_6-C_{14})$-arylidene, $(C_3-C_{13})$-heteroarylidene or $(C_6-C_{14})$-aryl-$(C_1-C_6)$-alkylidene, which can optionally be substituted, or

[CHR(3)]$_n$, in which, n is 1–8;

the radicals R(3) independently of one another are hydrogen, $(C_1-C_6)$-alkyl, $(C_3-C_8)$-cycloalkyl, $(C_6-C_{14})$-aryl or $(C_3-C_{13})$-heteroaryl, which, with the exception of the hydrogen, are in each case unsubstituted or monosubstituted by amino, substituted amino, amidino, substituted amidino, hydroxyl, carboxyl, carbamoyl, guanidino, substituted guanidino, ureido, substituted ureido, mercapto, methyl-mercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, or in which R(2) and R(3), together with the atoms carrying these, form a mono-, bi- or tricyclic ring system having 2 to 15 carbon atoms;

A is as defined for P;

B is a basic amino acid in the L- or D-configuration, which can be substituted in the side chain;

C is a compound of the formula IIIa or IIIb

 

in which, p is 2 to 8 and the radicals G' independently of one another are a radical of the formula IV

in which,

R(4) and R(5), together with the atoms carrying these, form a heterocyclic mono-, bi or tricyclic ring system having 2 to 15 carbon atoms;

E is the radical of a neutral, acid or basic, aliphatic or alicyclic-aliphatic amino acid;

the radicals F independently of one another are a radical of a neutral, acid or basic, aliphatic or aromatic amino acid, which can be substituted in the side chain, or a direct bond;

(D)Q is D-Tic, D-Phe, D-Dic, D-Thi or D-Nal, which can optionally be substituted by halogen, methyl or methoxy, or a radical of the formula (V)

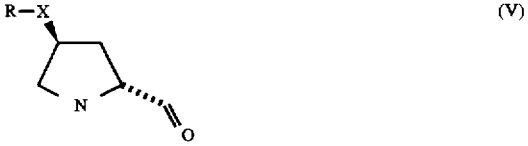

in which;

X is oxygen, sulfur or a direct bond;

R is hydrogen, $(C_1-C_8)$-alkyl, $(C_3-C_8)$-cycloalkyl, $(C_6-C_{14})$-aryl or $(C_6-C_{14})$-aryl-$(C_1-C_4)$-alkyl, in which the alicyclic radical can optionally be substituted by halogen, methyl or methoxy;

G is as defined above for G' or a direct bond;

F' is as defined above for F, a radical —NH—$(CH_2)_q$— where q is 2 to 8, or, if G is not a direct bond, a direct bond;

I is —OH, —NH$_2$ or NHC$_2$H$_5$;

K is a radical —NH(CH$_2$)$_x$—CO— where x is 1 to 4, or a direct bond; and

M is as defined above for F;

or a physiologically tolerated salt thereof.

15. A process for the preparation of the composition of claim 14, comprising the step of combining the bradykinin antagonist, or a physiologically tolerated salt thereof, and the other antiviral agent.

* * * * *

UNITED STATES PATENT AND TRADEMARK OFFICE
CERTIFICATE OF CORRECTION

PATENT NO.    : 5,789,383
DATED         : August 4, 1998
INVENTOR(S)   : Klaus Wirth et al.

It is certified that error appears in the above-identified patent and that said Letters Patent is hereby corrected as shown below:

<u>Title page,</u>
Item [75], Inventors, after "Liederbach", insert -- , both Germany --, and after "Graz", insert -- Austria --.

<u>Column 11,</u>
Line 5, after "or $a_2$)", insert -- in claim 3 --.
Line 47, "$a_1$)" should read -- $a_3$) --.

Signed and Sealed this

Twenty-third Day of September, 2003

JAMES E. ROGAN
*Director of the United States Patent and Trademark Office*